United States Patent [19]
Yamamoto et al.

[11] Patent Number: 5,759,445
[45] Date of Patent: Jun. 2, 1998

[54] LIPID-DISPERSED SOLUTION AND PROCESS FOR PRODUCING THE SAME

[75] Inventors: Tomohiro Yamamoto, Neyagawa; Toshihiko Yoshioka, Osaka; Shiro Nankai, Hirakata, all of Japan

[73] Assignee: Matsushita Electric Industrial Co., Ltd., Osaka-fu, Japan

[21] Appl. No.: 641,765

[22] Filed: May 2, 1996

[30] Foreign Application Priority Data

May 24, 1995 [JP] Japan ................... 7-124847

[51] Int. Cl.$^6$ ................. B01J 13/00; C12Q 1/60
[52] U.S. Cl. ................. 252/314; 252/311; 252/408.1; 436/13
[58] Field of Search ................. 252/311, 312, 252/314, 408.1; 436/13

[56] References Cited

U.S. PATENT DOCUMENTS

| | | | |
|---|---|---|---|
| 2,062,782 | 12/1936 | Epstein et al. | 252/311 X |
| 2,362,013 | 11/1944 | Lautenschläger et al. | 252/311 |
| 3,361,680 | 1/1968 | Bohrer | 252/314 |
| 3,505,074 | 4/1970 | Pardun | 252/312 X |
| 4,115,313 | 9/1978 | Lyon et al. | 252/312 X |
| 4,200,551 | 4/1980 | Orthoefer | 252/312 |
| 4,289,649 | 9/1981 | Harders et al. | 436/13 |
| 4,290,774 | 9/1981 | Girgis et al. | 436/13 |
| 4,343,897 | 8/1982 | Neumann et al. | 252/312 X |

FOREIGN PATENT DOCUMENTS 57-84356   5/1982   Japan.

*Primary Examiner*—Richard D. Lovering
*Attorney, Agent, or Firm*—Panitch Schwarze Jacobs & Nadel, P.C.

[57] ABSTRACT

There is disclosed an aqueous dispersed solution as a standard solution for determining lipid levels, having a dispersion form and a particle size, which are similar to those of serum lipids. A lipid-dispersed solution is obtained by evaporating an organic solvent from a mixture prepared by adding cholesterol, a phospholipid, a bile acid or bile acid salt, and a neutral lipid and/or a cholesterol ester in the organic solvent, swelling the resultant thin-film like mixture with water or buffer heated at a temperature higher than a phase transition temperature of the lecithin, and then dispersing the solution by a physical shear force. There can be easily obtained a solution having a cholesterol concentration of about less than 1,000 mg/dl, which is extremely stable and can be stored for a long period of time.

4 Claims, No Drawings

LIPID-DISPERSED SOLUTION AND PROCESS FOR PRODUCING THE SAME

BACKGROUND OF THE INVENTION

1. Field of the Invention

The present invention relates to an aqueous dispersed solution as a standard solution for determining the content of lipids, and a process for producing the same.

2. Description of the Prior Art

Determination of lipid levels in a body fluid, particularly determination of cholesterol levels, has rapidly come into wide use with the recent development of an enzymatic determination process, and its utility in the field of clinical diagnosis has been increasing. Therefore, a proper standard solution for determination of lipid levels is required. However, it is essentially difficult to dissolve lipids in water and, therefore, those dissolved in an organic solvent are exclusively used. For this, the lipid in these standard solutions differs in the existing state and fluid property from the lipid in the humor such as serum. This causes a great difference in reactivity between the standard solution and the body fluid (e.g., serum) as a specimen, which results in error in determined value.

Therefore, human- or animal- derived serum or purified lipoprotein cholesterol has been used as the standard solution. The process for purifying lipoprotein cholesterol is described, for example, in Japanese Laid-Open Patent Publication No. 56-101555. However, in the process using sera, it is difficult to obtain sera at a cheap price and, at the same time, there is a fear of an influence of unknown impurities on the determined value. The process for purifying lipoproteins has also a problem of complexity.

In order to improve these drawbacks, those which are solubilized in water with a surfactant have been used as the standard solution. However, a large amount of the surfactant is required for the solubilization of lipids in water. Therefore, the viscosity of the solution prepared by this process becomes high and its handling is sometimes difficult.

In order to solve this problem, it is suggested to use a mixture of a surfactant and lipids, which are different in HLB value (e.g., Japanese Laid-Open Patent Publication No. 57-84356). However, regarding the solution obtained by this process, the enzymatic reaction is sometimes inhibited by the surfactant present in the solution in the above enzymatic determination process. Since the lipid dispersion form is different from that in serum, the solution is not sometimes suitable as the standard solution according to the determination process.

As described above, various processes for stably dissolving or dispersing lipids in a simple procedure have been studied.

However, the fact that the dispersion form of lipids is largely different from that in serum as described above sometimes becomes a problem which hinders the use of the solution as the standard solution for calibrating a device. Taking this point into consideration, a process for dispersing lipids using the surfactant is also used. However, there is a problem that a high concentration of cholesterol, which is generated physiologically, can not be dispersed stably when a surfactant may be used.

SUMMARY OF THE INVENTION

The present inventors have studied intensively in order to solve the above problems. As a result, it is found that a dispersed solution shows excellent characteristics as a cholesterol standard solution, which is obtained by evaporating an organic solvent from a mixture prepared by adding cholesterol, lecithin, a surfactant and a neutral lipid, and/or a cholesterol ester in the organic solvent in a specific range of the concentration ratio, swelling the resultant thin-film like mixture with water or a buffer solution heated at a temperature higher than a phase transition temperature of the lecithin, and then dispersing the solution by ultrasonic irradiation.

The present invention provides a lipid-dispersed solution comprising a bile acid or a salt thereof, and a phospholipid, cholesterol and at least one member selected from the group consisting of a cholesterol ester and a neutral lipid as the lipids, and water or an aqueous solvent as a dispersing medium, the bile acid or the salt thereof and the lipids being dispersed in the water or aqueous solvent.

The present invention also provides a process for producing a lipid-dispersed solution, which comprises the steps of dissolving bile acid or a salt thereof and lipids in an organic solvent, evaporating the organic solvent from the resultant solution, and adding water or an aqueous solvent to the residual solid content to apply a physical shear force.

It is preferred that the step of applying the physical shear force is conducted under a deoxygenated atmosphere.

In addition, it is preferred that the step of evaporating the organic solvent is conducted at a temperature where the bile acid or salt thereof and the lipids can be dissolved in the organic solvent.

The lipids comprise a phospholipid, cholesterol, and at least one member selected from the group consisting of a cholesterol ester and a neutral lipid.

In one embodiment of the present invention, it is preferred that cholesterol linoleate is used as the cholesterol and cholesterol ester, lecithin is used as the phospholipid, sodium taurodeoxycholate is used as the bile acid salt, and tristearin is used as the neutral lipid. It is also preferred that a weight ratio of the sum of the cholesterol and cholesterol ester to the lecithin is from 1:1 to 1:4, a weight ratio of bile acid salt to the lecithin is from 1:1 to 1:20, a weight ratio of the neutral lipid to the lecithin is from 1:10 to 1:5, and a concentration of the lecithin is not more than 1,000 mg/dl when the lecithin is finally dispersed in water or buffer.

The cholesterol standard solution prepared by the above process has a dispersion form and a particle size, which are similar to those of serum lipids, and can provide a dispersed solution having a concentration of the sum of the cholesterol and cholesterol ester of about less than 1,000 mg/dl. The cholesterol-dispersed solution thus prepared is extremely stable and can be stored for a long period of time.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF PREFERRED EMBODIMENTS

The following Examples further illustrate the present invention in detail but are not construed to limit the scope thereof.

EXAMPLE 1

Sixty (60) mg of cholesterol, 90 mg of phosphatidyl choline as the phospholipid, 18 mg of tristearin as the neutral lipid and 4.5 mg of sodium cholate as the bile acid salt were dissolved in 1 ml of 2-propanol as the organic solvent. The resultant solution was charged in a glass container such as a test tube which was rotated using a rotary evaporator, and then 2-propanol was evaporated under reduced pressure. Thus, a thin film as a homogeneous mixture of cholesterol, phosphatidyl choline, tristearin and sodium cholate was formed on the inner wall of the glass container.

The step of evaporating 2-propanol to form the thin film may be conducted by spraying an inert gas (e.g., nitrogen or argon) to the above solution in place of vacuum evaporation by a rotary evaporator. In such way, oxidation of the phospholipids and neutral lipids in the step of forming the thin film can be prevented by evaporating the solvent under deoxygenated atmosphere.

Water or phosphate buffer as the aqueous solvent heated to the temperature higher than a phase transition temperature of phosphatidyl choline was added to the glass container in which the thin film was formed on the inner wall and the thin film was swollen. Then, an ultrasonic wave was irradiated by an ultrasonic crusher in order to apply a physical shear force and the above thin film was dispersed in water or phosphate buffer. A diameter of dispersed lipid particles varied depending on the output and irradiation time of the ultrasonic wave. Finally, lipid particles having a diameter of about 50 nm was obtained.

As the process for applying the physical shear force so as to disperse the thin film, a French press can also be used in place of the ultrasonic crusher.

In the present Example, sodium cholate as the surfactant is also dissolved in 2-propanol so that it can be contained uniformly in the thin film. When sodium cholate is not added to the 2-propanol solution and is added in the step of swelling and dispersing the thin film, a solution having a desirable particle size can not be obtained.

EXAMPLE 2

Fifteen (15) mg of cholesterol, 90 mg of phosphatidyl choline as the phospholipid, 45 mg of cholesterol linoleate as the cholesterol ester and 4.5 mg of deoxycholic acid as the bile acid were dissolved in 1 ml of 2-propanol as the organic solvent. A cholesterol standard solution containing ester type cholesterol such as cholesterol linoleate was obtained by charging the resultant solution in a glass container such as a test tube and dispersing the solution in water or an aqueous solvent in the same manner as that described in Example 1.

EXAMPLE 3

Fifteen (15) mg of cholesterol, 90 mg of phosphatidyl choline as the phospholipid, 45 mg of cholesterol linoleate as the cholesterol ester, 18 mg of tristearin as the neutral lipid and 4.5 mg of sodium taurodeoxycholate as the bile acid salt were dissolved in 1 ml of 2-propanol as the organic solvent. The resultant solution was charged in a glass container such as a test tube which was rotated using a rotary evaporator, and then 2-propanol was evaporated under reduced pressure. Thus, a thin film as a homogeneous mixture of cholesterol, phosphatidyl choline, tristearin and sodium cholate was formed on the inner wall of the glass container.

It is necessary to heat the glass container to about 60° C. when the solvent is evaporated to form a thin film. When the temperature is about room temperature, the above solution rapidly forms a white precipitate. The temperature at the time of forming the thin film must be the temperature at which the cholesterol, phospholipid, cholesterol ester, neutral lipid and bile acid salt, as the solute, can exist without depositing and precipitating. Accordingly, it is necessary to pay attention to the fact that the optimum temperature for forming the thin film varies depending on the combination and amount of the solutes.

A cholesterol standard solution containing ester type cholesterol such as cholesterol linoleate and a neutral lipid such as tristearin was obtained by adding water or a buffer solution to the thin film formed by the above process and dispersing in the same manner as that described in Example 1.

Regarding the form of lipid particles of the cholesterol standard solution obtained by this process, ester type cholesterol and a neutral lipid, which have a strong hydrophobic nature, exist in the central part of the particles, and phospholipid and cholesterol, a hydrophilic side chain of which exists outside, form the surface of the lipid particles so as to cover the ester type cholesterol and neutral lipid. Such a form is similar to that of lipids in the blood.

In the above Examples, phosphatidyl choline is used as the phospholipid, cholesterol linoleate is used as the cholesterol ester, tristearin which is one sort of triglycerides is used as the neutral lipid, sodium cholate and sodium taurodeoxycholate are used as the bile acid salt, and taurodeoxycholic acid is used as the bile acid, but they are not limited thereto.

As the phospholipid, for example, phosphatidyl choline, phosphatidyl serine, phosphatidyl glycerol, phosphatidyl inositol, phosphatidic acid, sphingomyelin and lysolecithin can be used alone or in combination.

As the bile acid or bile acid salt, for example, cholic acid, taurodeoxycholic acid, taurocholic acid, deoxycholic acid, glycocholic acid, glycodeoxycholic acid and a sodium salt thereof can be used alone or in combination.

As the neutral lipid, for example, triglycerides (e.g., tristearin, tripalmitin, etc.), of which constituent fatty acid has about 9 to 17 carbon atoms, can be used. As the cholesterol ester, for example, those having a fatty side chain, of which hydrocarbon group has 18 or less carbon atoms, can be used.

The effect of the present invention is not damaged even if a bile acid is used in place of the bile acid salt in the Example which uses the bile acid salt, and the bile acid salt is used in place of the bile acid in the Examples which use the bile acid.

As the organic solvent for dissolving the lipid so as to form the thin film, 2-propanol is used, but there can be used any organic solvent which can dissolve the phospholipid, cholesterol, bile acid or bile acid salt, cholesterol ester and neutral lipid, such as alcohol (e.g., 2-propanol, ethanol, methanol, etc.), diethyl ether, isopropyl ether, chloroform, dichloromethane, etc.

As described above, according to the present invention, there can be easily obtained a dispersed solution having the dispersion form and particle size, which are similar to those of serum lipids, and a high concentration of the sum total of the cholesterol and cholesterol ester, such as about less than 1,000 mg/dl. In addition, the cholesterol-dispersed solution thus prepared is extremely stable and can be stored at room temperature for a long period of time.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A process for producing a lipid-dispersed solution, which comprises the steps of dissolving a bile acid or a salt thereof and lipids in an organic solvent, wherein the lipids comprise a phospholipid, cholesterol and at least one member selected from the group consisting of a cholesterol ester and a neutral lipid, evaporating the organic solvent from the resultant solution at a temperature where the bile acid or the salt thereof and the lipids can be dissolved in the organic solvent, adding water or an aqueous solvent to the residual solid content, and applying a physical shear force.

2. The process for producing a lipid-dispersed solution in accordance with claim 1, wherein the step of applying the physical shear force is a step of irradiating with an ultrasonic wave.

3. The process for producing a lipid-dispersed solution in accordance with claim 1, wherein the step of evaporating the organic solvent is conducted under a deoxygenated atmosphere.

4. The process for producing a lipid-dispersed solution in accordance with claim 1, wherein a weight ratio of a sum of cholesterol and cholesterol ester to phospholipid is from 1:1 to 1:4, a weight ratio of bile acid salt to phospholipid is from 1:1 to 1:20, and a weight ratio of neutral lipid to phospholipid is from 1:10 to 1:5.

* * * * *